United States Patent
Ichimura et al.

(10) Patent No.: US 10,283,555 B2
(45) Date of Patent: May 7, 2019

(54) RADIATION DETECTION APPARATUS, MANUFACTURING METHOD THEREFOR, AND RADIATION DETECTION SYSTEM

(71) Applicant: CANON KABUSHIKI KAISHA, Tokyo (JP)

(72) Inventors: Tomoaki Ichimura, Kitamoto (JP); Satoshi Okada, Tokyo (JP); Kazumi Nagano, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 177 days.

(21) Appl. No.: 15/053,045

(22) Filed: Feb. 25, 2016

(65) Prior Publication Data

US 2016/0181308 A1    Jun. 23, 2016

Related U.S. Application Data

(63) Continuation of application No. PCT/JP2014/003730, filed on Jul. 15, 2014.

(30) Foreign Application Priority Data

Sep. 6, 2013   (JP) ................................. 2013-185703

(51) Int. Cl.
*H01L 27/146*   (2006.01)
*A61B 6/00*   (2006.01)

(52) U.S. Cl.
CPC ...... *H01L 27/14663* (2013.01); *A61B 6/4233* (2013.01); *A61B 6/461* (2013.01);
(Continued)

(58) Field of Classification Search
None
See application file for complete search history.

(56) References Cited

U.S. PATENT DOCUMENTS 7,391,029 B2   6/2008   Takeda et al.
7,564,112 B2   7/2009   Takeda
(Continued)

FOREIGN PATENT DOCUMENTS

JP   2004-296656   10/2004
JP   2005-197729 A   7/2005
(Continued)

OTHER PUBLICATIONS

U.S. Appl. No. 15/047,928, filed Feb. 19, 2016.
Office Action dated Jul. 28, 2017 in counterpart Japanese patent application 2013-185703, with translation.

*Primary Examiner* — Matthew L Reames
*Assistant Examiner* — Steven B Gauthier
(74) *Attorney, Agent, or Firm* — Venable LLP (57) ABSTRACT

A radiation detection apparatus employs a sensor panel having first and second opposing surfaces with a pixel array and electrical contacts arranged on the first surface side. A first supporting portion is secured to the panel with an adhesive layer, and supports the pixel array from the second surface side of the panel. A second supporting portion is fixed to the panel so as to inhibit the second supporting portion from being removed from the panel. The second supporting portion supports the electrical contacts from the second surface side of the panel. The elastic modulus of the second supporting portion is higher than that of the adhesive layer, and a number of wiring members are pressure-bonded to the electrical contacts.

10 Claims, 6 Drawing Sheets

(52) U.S. Cl.
CPC .......... *A61B 6/52* (2013.01); *H01L 27/14618* (2013.01); *H01L 27/14636* (2013.01); *H01L 27/14683* (2013.01); *H01L 2924/0002* (2013.01)

(56) References Cited

U.S. PATENT DOCUMENTS

| | | | |
|---|---|---|---|
| 7,595,493 B2 | 9/2009 | Okada et al. | |
| 7,723,693 B2 | 5/2010 | Okada et al. | |
| 8,653,465 B2 | 2/2014 | Nagano et al. | |
| 8,704,185 B2 | 4/2014 | Ishida et al. | |
| 8,957,383 B2 | 2/2015 | Sasaki et al. | |
| 9,006,665 B2 | 4/2015 | Nagano et al. | |
| 9,052,400 B2 | 6/2015 | Saruta et al. | |
| 9,054,012 B2 | 6/2015 | Nomura et al. | |
| 2002/0195568 A1* | 12/2002 | Mori | H01L 27/14663 250/370.11 |
| 2004/0178350 A1* | 9/2004 | Nagano | G01T 1/2018 250/370.11 |
| 2004/0195514 A1* | 10/2004 | Nagano | G01T 1/2018 250/370.11 |
| 2007/0131867 A1* | 6/2007 | Okada | G01T 1/2018 250/370.09 |
| 2007/0257198 A1* | 11/2007 | Ogawa | G01T 1/2002 250/370.11 |
| 2008/0290285 A1 | 11/2008 | Wakamatsu | |
| 2012/0320310 A1* | 12/2012 | Adachi | G02B 5/045 349/64 |
| 2013/0168559 A1 | 7/2013 | Saruta et al. | |
| 2013/0308755 A1 | 11/2013 | Ishida et al. | |
| 2013/0341516 A1 | 12/2013 | Ishida et al. | |
| 2014/0353515 A1* | 12/2014 | Fujita | H04N 5/32 250/370.09 |

FOREIGN PATENT DOCUMENTS

| | | |
|---|---|---|
| JP | 2006-148005 A | 6/2006 |
| JP | 2008-026013 A | 2/2008 |
| JP | 4464260 B | 5/2010 |

\* cited by examiner

RADIATION DETECTION APPARATUS, MANUFACTURING METHOD THEREFOR, AND RADIATION DETECTION SYSTEM

This application is a continuation of International Patent Application No. PCT/JP2014/003730 filed on Jul. 15, 2014, and claims priority to Japanese Patent Application No. 2013-185703 filed on Sep. 6, 2013, the entire content of both of which is incorporated herein by reference.

TECHNICAL FIELD

The present invention relates to a radiation detection apparatus, a manufacturing method therefor, and a radiation detection system.

BACKGROUND ART

Japanese Patent No. 4464260 has proposed a technique associated with a radiation imaging apparatus including a sensor panel having a plurality of photoelectric conversion elements and a scintillator layer. The sensor panel includes electrical contacts electrically connected to the photoelectric conversion elements. Wiring members for reading out signals from the sensor panel to the outside are connected to the electrical contacts. The wiring members are pressure-bonded to the electrical contacts. A supporting substrate is adhered to the reverse surface of the sensor panel with an adhesive agent. Gaps are provided between the supporting substrate and portions, of the sensor panel, on which the electrical contacts are arranged. When pressure-bonding the wiring members, rigid members are inserted into the gaps. After the wiring members are mounted, the rigid members are removed from the gaps, and buffer members are inserted instead of the rigid members. When pressure-bonding the wiring members, mounting the rigid members suppresses the deformation of the sensor panel which is caused by pressure-bonding, and mounting the buffer members in the other case improves the impact resistance of the sensor panel.

SUMMARY OF INVENTION

Technical Problem

The radiation imaging apparatus disclosed in Japanese Patent No. 4464260 is configured to replace rigid members with buffer members in the gaps between the supporting substrate and the portions, of the sensor panel, on which the electrical contacts are arranged. In this arrangement, when these members are inserted and removed, the sensor panel may be damaged. Some aspects of the present invention provide a technique for suppressing damage/deformation of a sensor panel when pressure-bonding wiring members in a radiation detection apparatus.

Solution to Problem

Some embodiments provide a method of manufacturing a radiation detection apparatus, the method comprising: preparing a sensor panel having a first surface and a second surface located on an opposite side to the first surface, with a pixel array and electrical contacts being arranged on the first surface side; adhering a first supporting portion to the sensor panel with an adhesive layer, the first supporting portion supporting the pixel array from the second surface side of the sensor panel; fixing a second supporting portion to the sensor panel so as to inhibit the second supporting portion from being removed from the sensor panel, the second supporting portion supporting the electrical contacts from the second surface side of the sensor panel; and pressure-bonding wiring members to the electrical contacts, wherein an elastic modulus of the second supporting portion in the pressure-bonding is higher than an elastic modulus of the adhesive layer in the pressure-bonding.

Further features of the present invention will become apparent from the following description of exemplary embodiments (with reference to the attached drawings).

BRIEF DESCRIPTION OF DRAWINGS

The accompanying drawings, which are incorporated in and constitute a part of the specification, illustrate embodiments of the invention and, together with the description, serve to explain the principles of the invention.

DESCRIPTION OF EMBODIMENTS

The embodiments will be described below with reference to the accompanying drawings. The same reference numerals denote the same elements throughout various embodiments, and a repetitive description of them will be omitted. In addition, the respective embodiments can be changed and combined as needed.

Figure 1A:
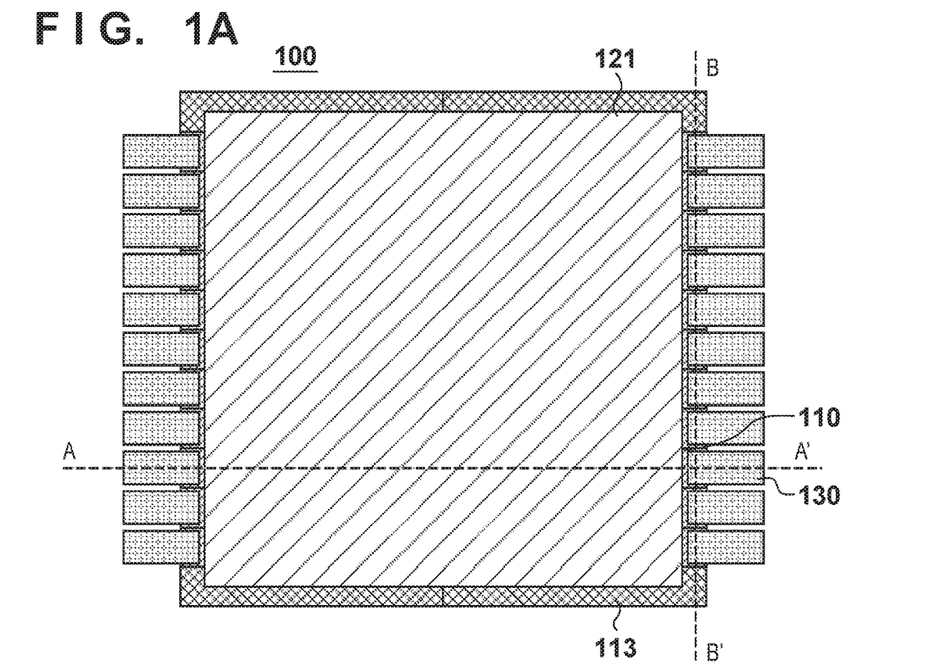
FIG. 1A is a view for explaining an example of the arrangement of a radiation detection apparatus according to some embodiments.
Figure 1B:
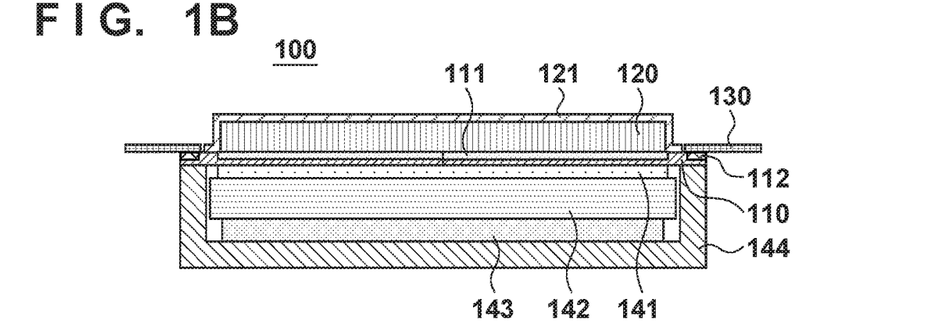
FIG. 1B is a view for explaining an example of the arrangement of the radiation detection apparatus according to some embodiments.
Figure 1C:
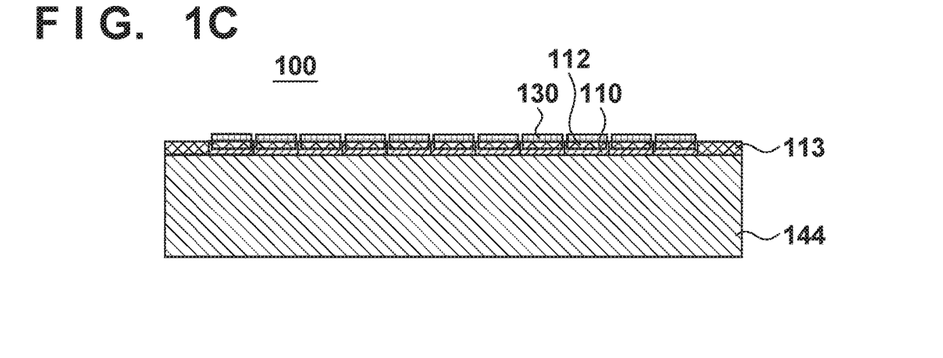
FIG. 1C is a view for explaining an example of the arrangement of the radiation detection apparatus according to some embodiments.

An example of the arrangement of a radiation detection apparatus 100 according to some embodiments will be described with reference to FIGS. 1A to 1C. FIG. 1A is a plan view of the radiation detection apparatus 100. FIG. 1B is a sectional view taken along a line A-A' of the radiation detection apparatus 100. FIG. 1C is a sectional view taken along a line B-B' of the radiation detection apparatus 100.

The radiation detection apparatus 100 includes constituent elements shown in FIGS. 1A to 1C. A sensor panel 110 includes a pixel array 111 and electrical contacts 112 on one principal surface (the surface on the upper side in FIG. 1B; to be referred to as the obverse surface hereinafter). The pixel array 111 has a plurality of pixels arranged in an array. Each pixel includes a photoelectric conversion element. The electrical contacts 112 are located on outer sides of the pixel array 111 and electrically connected to the pixel array 111. In the case shown in FIGS. 1A to 1C, the plurality of electrical contacts 112 are arranged along two opposite sides of the radiation detection apparatus 100. However, the electrical contacts 112 may be arranged on two adjacent sides, only one side, three sides, or all the sides. In addition, in the case shown in FIGS. 1A to 1C, the sensor panel 110 is constituted by a plurality of sensor chips each having the pixel array 111 and the electrical contact 112. Dummy chips 113, each having no pixel array 111 or electrical contact 112, are arranged around the plurality of sensor chips. Alternatively, the sensor panel 110 may be constituted by one sensor chip.

The sensor panel 110 has any arrangement as long as it includes the pixel array 111 and the electrical contacts 112. For example, the sensor panel 110 may be a CMOS sensor or CCD sensor having semiconductor elements formed on a silicon substrate. Alternatively, the sensor panel 110 may be a flat panel having semiconductor elements formed on a substrate such as a glass substrate.

The radiation detection apparatus 100 may be of a front-side illumination type (a type that radiation enters from the obverse surface of the sensor panel 110) or back-side illumination type (a type that radiation enters from the reverse surface of the sensor panel). The reverse surface of the sensor panel 110 is a principal surface (the surface on the lower side in FIG. 1B) on the opposite side of the sensor panel 110 to the obverse surface. In general, when using the radiation detection apparatus for mammography, imaging is performed by using X-rays at a low tube voltage of about 25 keV. When the radiation detection apparatus 100 is of the back-side illumination type, it is possible to use a thin flat substrate to suppress radiation absorption by the substrate of the sensor panel 110, assuming that the apparatus is used for mammography.

Table 1 given below shows the results obtained by calculating X-ray transmittance improvement ratios at a tube voltage of 25 keV on single-crystal silicon substrates with various thicknesses with reference to the transmittance of a single-crystal silicon substrate with a thickness of 0.775 mm, which is the thickness of a general 300-mm wafer.

TABLE 1

| Thickness of Substrate | X-ray Transmittance Improvement Ratio (with reference to thickness of 0.775 mm) |
|---|---|
| 0.5 mm | 10.2% |
| 0.3 mm | 18.5% |
| 0.2 mm | 39.2% |

In addition, Table 2 given below shows the results obtained by calculating X-ray transmittance improvement ratios at a tube voltage of 25 keV on single-crystal silicon substrates with various thicknesses with reference to the transmittance of a 0.7-mm thick glass substrate.

TABLE 2

| Thickness of Substrate | X-ray Transmittance Improvement Ratio (with reference to thickness of 0.7 mm) |
|---|---|
| 0.5 mm | 10.0% |
| 0.3 mm | 21.8% |
| 0.2 mm | 35.5% |

In either of the above cases, it is obvious that an X-ray transmittance improves with a reduction in the thickness of a substrate.

The sensor panel 110 may have a protective layer on the obverse surface side to cover and protect the pixel array 111. The protective layer is formed from, for example, an organic resin. For example, a high heat-resistant organic resin is used. Such organic resins include a polyimide resin, styrene resin, epoxy-based resin, acrylic-based resin, polyvinylidene chloride-based resin, polyvinylidene fluoride-based resin, polyester-based resin, and polyolefin-based resin.

A scintillator layer 120 is arranged on the obverse surface side of the sensor panel 110 at a position to cover the pixel array 111. The scintillator layer 120 converts radiation entering the radiation detection apparatus 100 into light (for example, visible light) having a wavelength that can be detected by each photoelectric conversion element of the pixel array 111. The scintillator layer 120 is formed from, for example, an alkali halide-based material typified by a material (CsI:Tl) obtained by doping cesium iodide (to be referred to as CsI hereinafter) with Tl. The scintillator layer 120 is formed from a powder phosphor (to be referred to as a GOS hereinafter) obtained by doping a metal oxysulfide (for example, $Gd_2O_2S$) as a matrix with a small amount of trivalent rare earth as a luminescent center such as terbium or europium.

The surface of the scintillator layer 120 may be covered by a scintillator protective layer 121 except for the surface in contact with the sensor panel 110. The scintillator protective layer 121 suppresses a decrease in the luminescence amount or sharpness of the scintillator layer 120 which is caused by moisture absorption. The scintillator protective layer 121 can be formed by bonding an organic resin having low moisture permeability or a sheet having low moisture permeability to it through an adhesive layer such as an adhesive agent, pressure sensitive adhesive agent, or the like. Organic resins having low moisture permeability include chlorine-based resins such as polyparaxylylene and polyvinylidene chloride and fluorine-based resins such as PCTFE and polyvinylidene fluoride. Sheets having low moisture permeability include metallic foils such as aluminum, silver, and copper foils as well as resin sheets. In the embodiment shown in FIGS. 1A to 1C, the scintillator protective layer 121 is formed by bonding an aluminum sheet to it using a pressure sensitive adhesive agent.

Wiring members 130 are mounted on the electrical contacts 112. The wiring members 130 are, for example, FPCs (Flexible Printed Circuits). The conductor members contained in the wiring members 130 are electrically connected to the electrical contacts 112. An external apparatus and the pixel array 111 exchange electrical signals via the wiring members 130 and the electrical contacts 112.

The reverse surface of the sensor panel 110 is adhered to the obverse surface of a supporting substrate 142 with an adhesive layer 141. The adhesive layer 141 is in contact with a portion, of the reverse surface of the sensor panel 110, on which the pixel array 111 is arranged but is not in contact with portions, of the revere surface, on which the electrical contacts 112 are arranged. Bonding the supporting substrate 142 to the sensor panel 110 can improve the strength of the sensor panel 110. In this manner, the supporting substrate 142 supports the pixel array 111 from the reverse surface side of the sensor panel 110. A high heat-resistant member may be used as the supporting substrate 142. When the radiation detection apparatus 100 is of the back-side illumination type, a member having high radiation transmittance may be used as the supporting substrate 142. Materials for such members include light metals and light metal alloys such as aluminum, magnesium, an aluminum alloy, and a magnesium alloy, crystals such as silicon, germanium, and carbon, amorphous materials such as amorphous carbon, glass, ceramics, and pottery materials, composite materials such as CFRP (Carbon Fiber Reinforced Plastic) and GFRP (Glass Fiber Reinforced Plastic), and heat-resistant resins such as an aramid-based resin, a polyimide-based resin, a PPS resin, a PEEK resin, an epoxy-based resin, and an acrylic-based resin. The adhesive layer 141 also functions as a buffer member.

The reverse surface of the supporting substrate 142 is bonded to the bottom portion of a box-like frame member 144 with an adhesive layer 143. Side walls of the frame member 144 are in contact with portions, of the reverse surface of the sensor panel 110, on which the electrical contacts 112 are arranged. The side walls of the frame member 144 therefore support the electrical contacts 112 from the reverse surface side of the sensor panel 110. In order to suppress the deformation of the sensor panel 110 at the time of mounting the wiring members 130, the frame member 144 has a higher elastic modulus than the adhesive layer 141. In this specification, an elastic modulus can be, for example, a volume elastic modulus. In addition, the compressive strength of the frame member 144 is equal to or more than 90 MPa (equal to or more than 918 kgf/cm²). If the compressive strength of the frame member 144 is less than 90 MPa, mounting the wiring members 130 on the electrical contacts 112 with a pressure of 5 MPa can deform the frame member 144 and cause a contact failure on the wiring members 130. The frame member 144 is formed from one of the following materials: metals and metal alloys such as aluminum, an aluminum alloy, magnesium, a magnesium alloy, iron, and stainless steel, crystals such as silicon, germanium, and carbon, amorphous materials such as amorphous carbon, glass, and ceramics, composite materials such as CFRP and GFRP, and resins such as an aramid-based resin, a polyimide-based resin, an acrylic-based resin, a polyethylene-based resin, a phenol-based resin, an acetylcellulose-based resin, and a vinyl chloride-based resin. Gaps exist between the side walls of the frame member 144 and the adhesive layer 141. In other words, the reverse surface of the sensor panel 110 includes portions, between the frame member 144 and the adhesive layer 141, which are covered by none of them. The sensor panel 110 is adhered to the supporting substrate 142 with the adhesive layer 141. The frame member 144 is adhered to the supporting substrate 142 with the adhesive layer 143. Therefore, the frame member 144 is fixed on the sensor panel 110. The frame member 144 cannot be removed from the radiation detection apparatus 100.

Figure 2A:
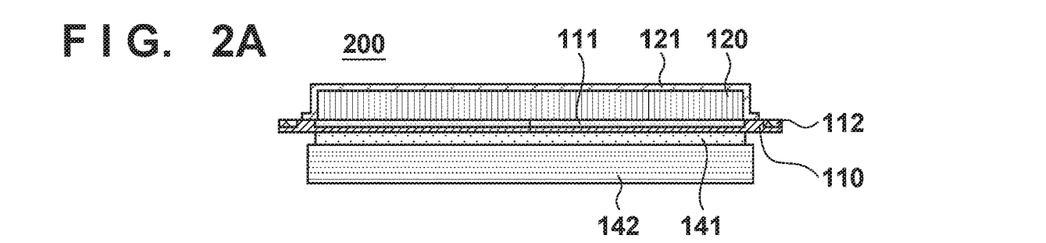
FIG. 2A is a view for explaining an example of a manufacturing method for the radiation detection apparatus in FIGS. 1A to 1C.

An example of a manufacturing method for the radiation detection apparatus 100 will be described next with reference to FIGS. 2A to 2D. First of all, as shown in FIG. 2A, the sensor panel 110 including the pixel array 111 and the electrical contacts 112 is prepared. This process can be performed by any technique and may be performed by using an existing technique. Therefore, a detailed description of the process will be omitted.

Subsequently, the reverse surface of the prepared sensor panel 110 may be polished by chemical polishing (etching) or the like to thin the substrate of the sensor panel 110. For example, the substrate of the sensor panel 110 may be polished to a thickness of 5 mm or less. Setting the thickness of a silicon substrate to, for example, 0.3 mm can improve the X-ray transmittance by 18.5% as compared with a silicon substrate having a thickness of 0.775 mm. In addition, when using a flat panel as the sensor panel 110, setting the thickness of the glass substrate of the sensor panel 110 to, for example, 0.3 mm can improve the X-ray transmittance by 21.8% as compared with a glass substrate having a thickness of 0.7 mm.

Subsequently, the reverse surface of the sensor panel 110 is adhered to the obverse surface of the supporting substrate 142 with the adhesive layer 141. The adhesive layer 141 is, for example, a 100-μm thick silicone-based pressure sensitive adhesive agent. The adhesive layer 141 is in contact with a portion, of the reverse surface of the sensor panel 110, on which the pixel array 111 is arranged but is not in contact with portions, of the reverse surface, on which the electrical contacts 112 are arranged.

Subsequently, the scintillator layer 120 is arranged on the obverse surface side of the sensor panel 110. The scintillator layer 120 is formed by, for example, heating and depositing CsI and TlI simultaneously in a vacuum chamber. For example, a resistance heating boat is filled with a phosphor material as a deposition material, and the sensor panel 110 is installed on the support holder of a deposition apparatus. The deposition apparatus is then evacuated by a vacuum pump. Ar gas is introduced into the apparatus to adjust the degree of vacuum to 0.1 Pa. The apparatus then performs deposition. When using a powder phosphor as the scintillator layer 120, the scintillator layer 120 is formed by coating and drying, for example, GOS.

Subsequently, the scintillator protective layer 121 covering the scintillator layer 120 is formed. The scintillator protective layer 121 is formed by bonding an aluminum sheet coated with a pressure sensitive adhesive agent to the scintillator layer 120 so as to cover it by using a roll laminator. As the scintillator protective layer 121, polyparaxylylene is formed by CVD. For example, the sensor panel 110 on which the scintillator layer 120 is formed is installed in a chamber for CVD, which is evacuated to 30 Pa. Polyparaxylylene is then deposited while the table on which the sensor panel 110 is installed is rotated at 5 rpm. With the above process, a structure 200 shown in FIG. 2A is formed.

Figure 2B:
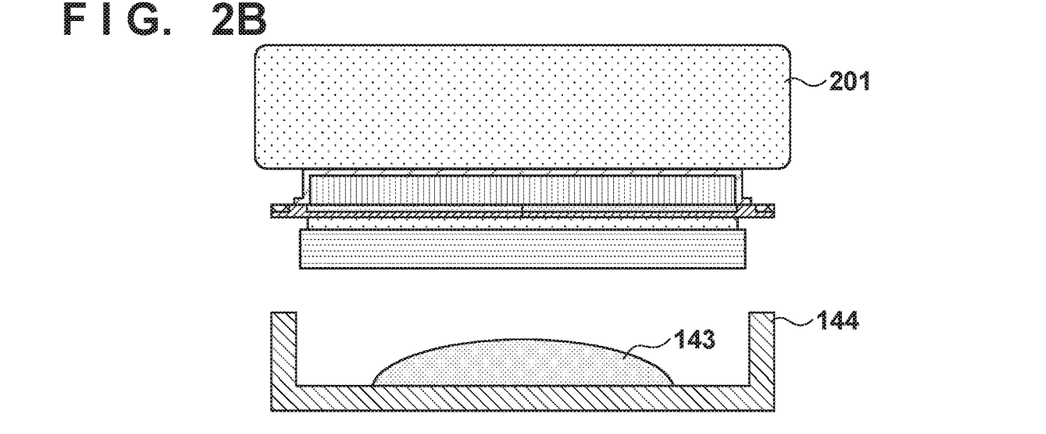
FIG. 2B is a view for explaining an example of the manufacturing method for the radiation detection apparatus in FIGS. 1A to 1C.

Subsequently, as shown in FIG. 2B, the bottom portion of the frame member 144 is coated with the adhesive layer 143, and a chuck stage 201 vacuum-chucks the upper side of the structure 200 (the upper surface of the scintillator protective layer 121). As the frame member 144, for example, a 2-mm thick CFRP plate processed into a box-like shape is used. The adhesive layer 143 is formed from, for example, a two-pack epoxy resin designed to promote curing by mixing two types of liquids. Using the two-pack epoxy resin can cure the adhesive layer 143 without heating it.

Figure 2C:
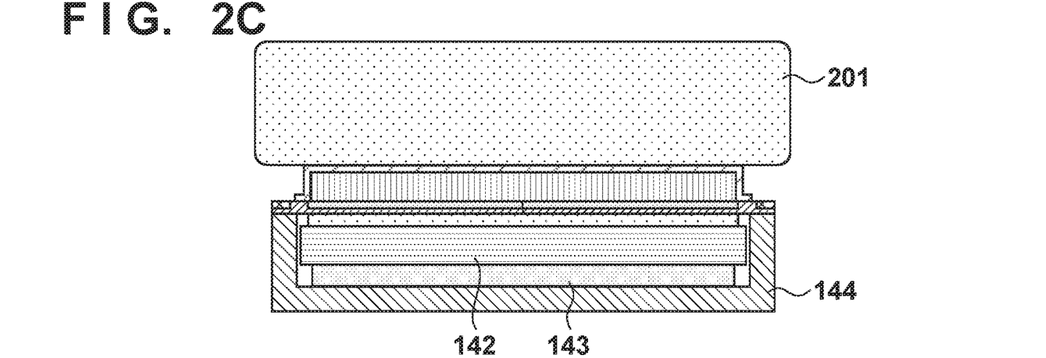
FIG. 2C is a view for explaining an example of the manufacturing method for the radiation detection apparatus in FIGS. 1A to 1C.

Subsequently, as shown in FIG. 2C, the structure 200 is mounted on the frame member 144. When performing this mounting operation, the structure 200 is pressurized with, for example, a pressure of 0.05 MPa. Applying an excessively high pressure at the time of the mounting operation may cause cracking in the sensor panel 110. Applying an excessively low pressure at the time of the mounting operation may make the contact between the sensor panel 110 and the frame member 144 insufficient and cause cracking in the sensor panel 110 when mounting the wiring members 130.

Figure 2D:
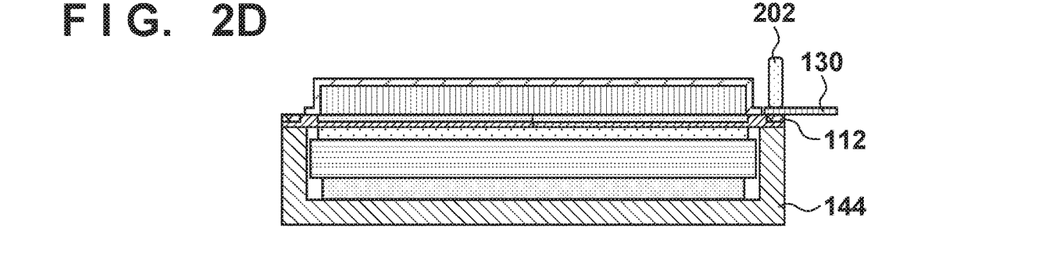
FIG. 2D is a view for explaining an example of the manufacturing method for the radiation detection apparatus in FIGS. 1A to 1C.

Subsequently, as shown in FIG. 2D, the wiring members 130 are arranged on the electrical contacts 112 through adhesive members such as anisotropic conductive films (ACFs), gold bumps, or the like. Thereafter, each wiring member 130 is thermally pressure-bonded to a corresponding one of the electrical contacts 112 by using a pressure-bonding head 202 at a temperature of 100° C. to 200° C. and a pressure of 1 MPa to 5 MPa for 5 sec to 5 min. When performing this thermal pressure-bonding, the frame member 144 supports portions, of the sensor panel 110, on which the electrical contacts 112 are arranged, from the reverse surface. In this process, the frame member 144 has a higher elastic modulus than the adhesive layer 141, and hence is hard to be deformed by a pressure from the pressure-bonding head 202. This can therefore suppress the deformation of the sensor panel 110 and improve the adhesiveness between the electrical contacts 112 and the wiring members 130. As a result, high-quality radiation images can be obtained from the radiation detection apparatus 100. The wiring members 130 may be adhered to the electrical contacts 112 by pressure-bonding without heating instead of using thermal pressure-bonding.

Figure 3A:
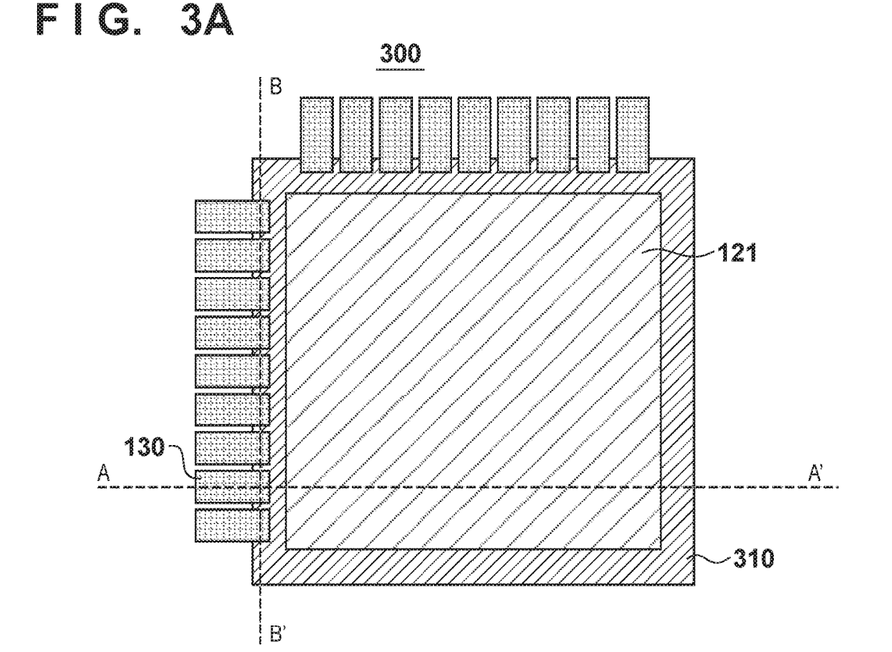
FIG. 3A is a view for explaining an example of the arrangement of a radiation detection apparatus according to some embodiments.
Figure 3B:
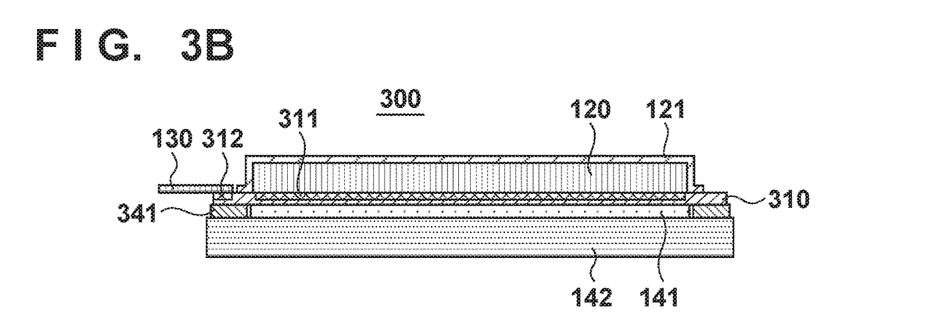
FIG. 3B is a view for explaining an example of the arrangement of the radiation detection apparatus according to some embodiments.
Figure 3C:
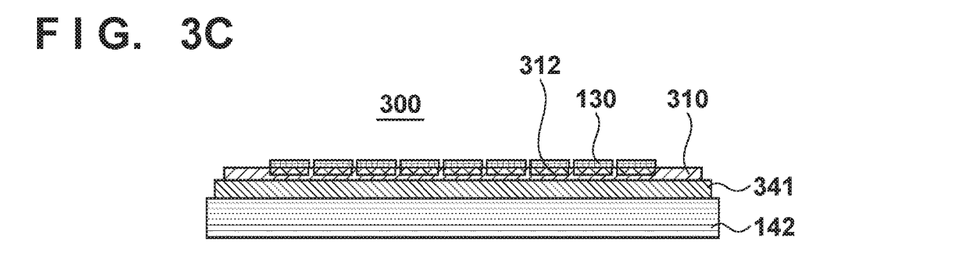
FIG. 3C is a view for explaining an example of the arrangement of the radiation detection apparatus according to some embodiments.

An example of the arrangement of a radiation detection apparatus 300 according to another embodiment will be described next with reference to FIGS. 3A to 3C. FIG. 3A is a plan view of the radiation detection apparatus 300. FIG. 3B is a sectional view taken along a line A-A' of the radiation detection apparatus 300. FIG. 3C is a sectional view taken along a line B-B' of the radiation detection apparatus 300.

The radiation detection apparatus 300 includes the respective constituent elements shown in FIGS. 3A to 3C. The same reference numerals denote constituent elements common to the radiation detection apparatus 300 and the radiation detection apparatus 100, and a repetitive description of them will be omitted. A sensor panel 310 has a pixel array 311 and electrical contacts 312 on one principal surface (the surface on the upper side in FIG. 3B; to be referred to as the obverse surface hereinafter). The pixel array 311 and the electrical contacts 312 may be the same as the pixel array 111 and the electrical contacts 112, respectively, and hence a description of them will be omitted. In the embodiment shown in FIGS. 3A to 3C, the sensor panel 310 is formed from one sensor chip. However, as in the case shown in FIGS. 1A to 1C, the sensor panel 310 may be constituted by a plurality of sensor chips.

A supporting member 341 is arranged between a supporting substrate 142 and portions, of the sensor panel 310, on which the electrical contacts 312 are arranged. That is, the supporting member 341 supports the electrical contacts 312 from the reverse surface side of the sensor panel 310. The supporting member 341 has a higher elastic modulus than an adhesive layer 141. In addition, as the supporting member 341, a material having a compressive strength of 90 MPa or more can be used. As such a material, for example, an organic resin such as an epoxy resin having a compressive strength of 150 MPa may be used. Alternatively, a metallic material such as a metal or metal alloy having a compressive strength of 90 MPa or more may be used as a material for the supporting member 341. For example, stainless steel having a compressive strength of 400 MPa is used as a material for the supporting member 341. In addition, a material having adhesiveness may be used as a material for the supporting member 341. That is, the supporting member 341 may be an adhesive layer which adheres the reverse surface sides of the electrical contacts 312 to the supporting substrate 142. Furthermore, a material for the supporting member 341 may have curability such as light curability or heat curability.

The radiation detection apparatus 300 can have the same advantages as those of the radiation detection apparatus 100. In addition, the radiation detection apparatus 300 can be manufactured at low cost because it has fewer constituent elements than the radiation detection apparatus 100.

Figure 4A:
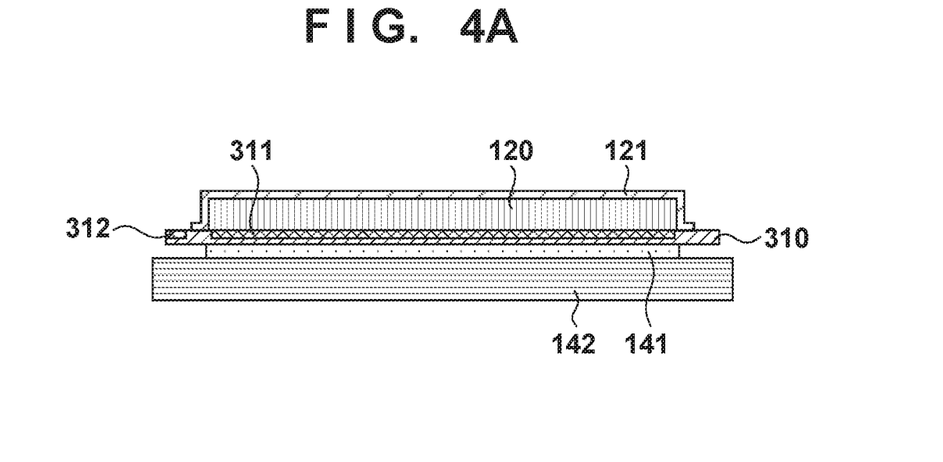
FIG. 4A is a view for explaining an example of a manufacturing method for the radiation detection apparatus in FIGS. 3A to 3C.

An example of a manufacturing method for the radiation detection apparatus 300 will be described next with reference to FIGS. 4A to 4C. First of all, as shown in FIG. 4A, the sensor panel 310 including the pixel array 311 and the electrical contacts 312 is prepared. This process can be performed by any technique and may be performed by using an existing technique. Therefore, a detailed description of the process will be omitted. Subsequently, as in the same manner as that described with reference to FIG. 2A, the sensor panel 310 is adhered to the supporting substrate 142 with the adhesive layer 141. A scintillator layer 120 and a scintillator protective layer 121 are then formed on the sensor panel 310.

Figure 4B:
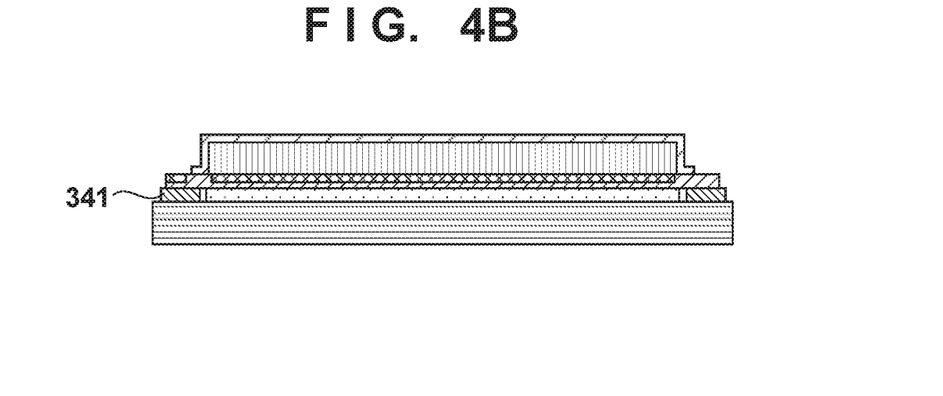
FIG. 4B is a view for explaining an example of the manufacturing method for the radiation detection apparatus in FIGS. 3A to 3C.

Subsequently, as shown in FIG. 4B, the supporting member 341 is inserted between the supporting substrate 142 and portions, of the sensor panel 310, on which the electrical contacts 312 are arranged. For example, an epoxy resin before curing is arranged between the supporting substrate 142 and the sensor panel 110 by using Dispenser MS-10 available from Musashi engineering. Thereafter, the epoxy resin is cured for 1 hr at 80° C. to form the supporting member 341.

Figure 4C:
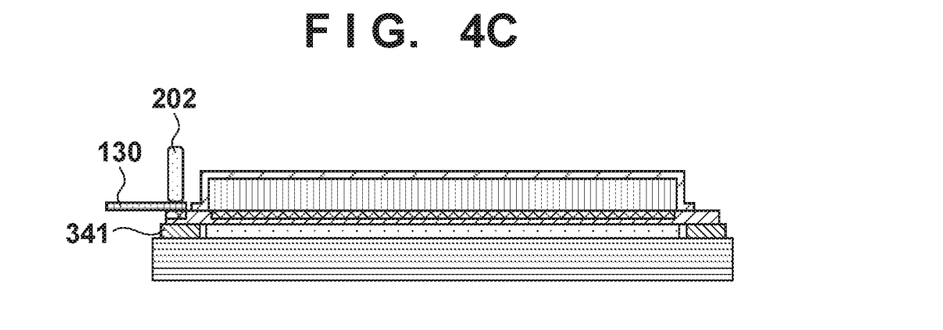
FIG. 4C is a view for explaining an example of the manufacturing method for the radiation detection apparatus in FIGS. 3A to 3C.

Subsequently, as shown in FIG. 4C, wiring members 130 are pressure-bonded to the electrical contacts 312. Since this process is the same as that shown in FIG. 2D, a repetitive description will be omitted. In the case shown in FIGS. 4A to 4C, the supporting member 341 is arranged after the sensor panel 310 is adhered to the supporting substrate 142. However, the sensor panel 310 may be adhered to the supporting substrate 142 after the supporting member 341 is arranged on the supporting substrate 142.

Figure 5A:
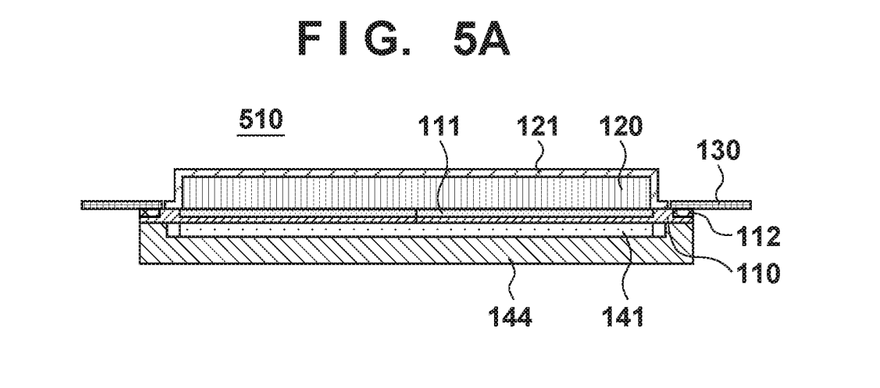
FIG. 5A is a view for explaining an example of the arrangement of a radiation detection apparatus according to some embodiments.

Examples of the arrangements of radiation detection apparatuses according to various other embodiments of the present invention will be described next with reference to FIGS. 5A to 5C. The same reference numerals denote constituent elements common to the radiation detection apparatuses described with reference to FIGS. 5A to 5C and the radiation detection apparatuses 100 and 300, and a repetitive description of them will be omitted. A radiation detection apparatus 510 in FIG. 5A has a sensor panel 110 directly adhered to a frame member 144 with an adhesive layer 141.

Figure 5B:
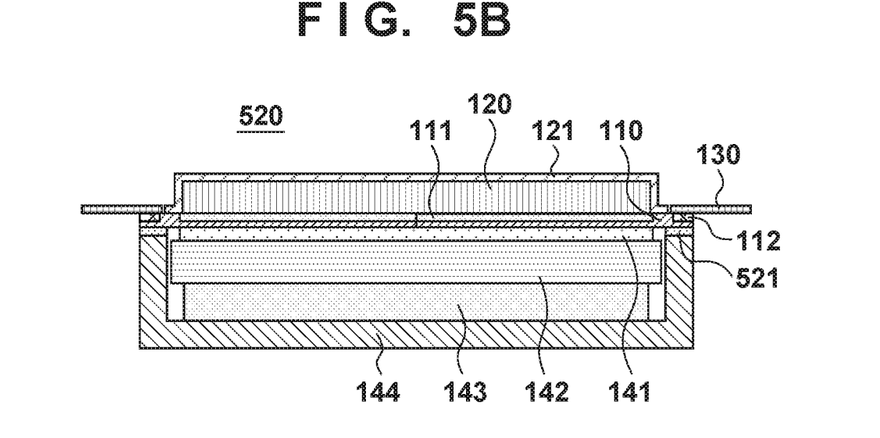
FIG. 5B is a view for explaining an example of the arrangement of the radiation detection apparatus according to some embodiments.

A radiation detection apparatus 520 in FIG. 5B has an adhesive layer 521 having curability arranged between a frame member 144 and portions, of the reverse surface of a sensor panel 110, on which electrical contacts 112 are arranged. Polishing the reverse surface of the sensor panel 110 sometimes causes irregularity such as polishing unevenness or polishing flaws caused by an abrasive on the reverse surface. The radiation detection apparatus 520 is configured to reduce such irregularity by using the adhesive layer 521. First of all, the adhesive layer 521 before curing is arranged between the frame member 144 and portions, of the reverse surface of the sensor panel 110, on which the electrical contacts 112 are arranged. Thereafter, the adhesive layer 521 is cured. The elastic modulus of the cured adhesive layer 521 is higher than that of an adhesive layer 141. Therefore, the adhesive layer 141 supports the electrical contacts 112 from the reverse surface side of the sensor panel 110. As a material for the adhesive layer, it is possible to use one of the following resins: an epoxy resin, an acrylic resin, a polyethylene-based resin, a phenol-based resin, an acetylcellulose-based resin, and a vinyl chloride-based resin.

Figure 5C:
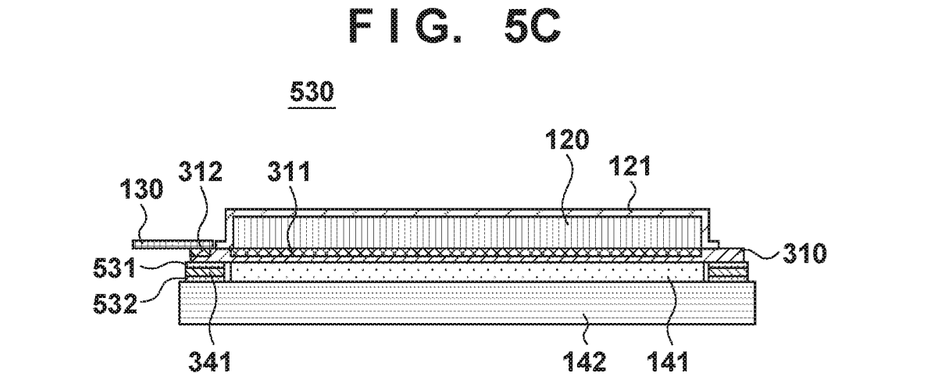
FIG. 5C is a view for explaining an example of the arrangement of the radiation detection apparatus according to some embodiments.

A radiation detection apparatus 530 in FIG. 5C is configured such that a supporting member 341 is adhered to a sensor panel 310 with an adhesive layer 531, and the supporting member 341 is adhered to a supporting substrate 142 with an adhesive layer 532. Since the adhesive layers 531 and 532 may each be the same as the adhesive layer 521, a repetitive description will be omitted.

In the above embodiments, the scintillator layer is directly formed on the sensor panel. However, a scintillator panel having a scintillator layer may be prepared independently of a sensor panel, and the sensor panel and the scintillator panel may be overlaid on each other to form a radiation detection apparatus. Alternatively, a radiation detection apparatus may be of a type that has no scintillator layer and makes the conversion elements of a sensor panel directly convert radiation into charge.

Figure 6:
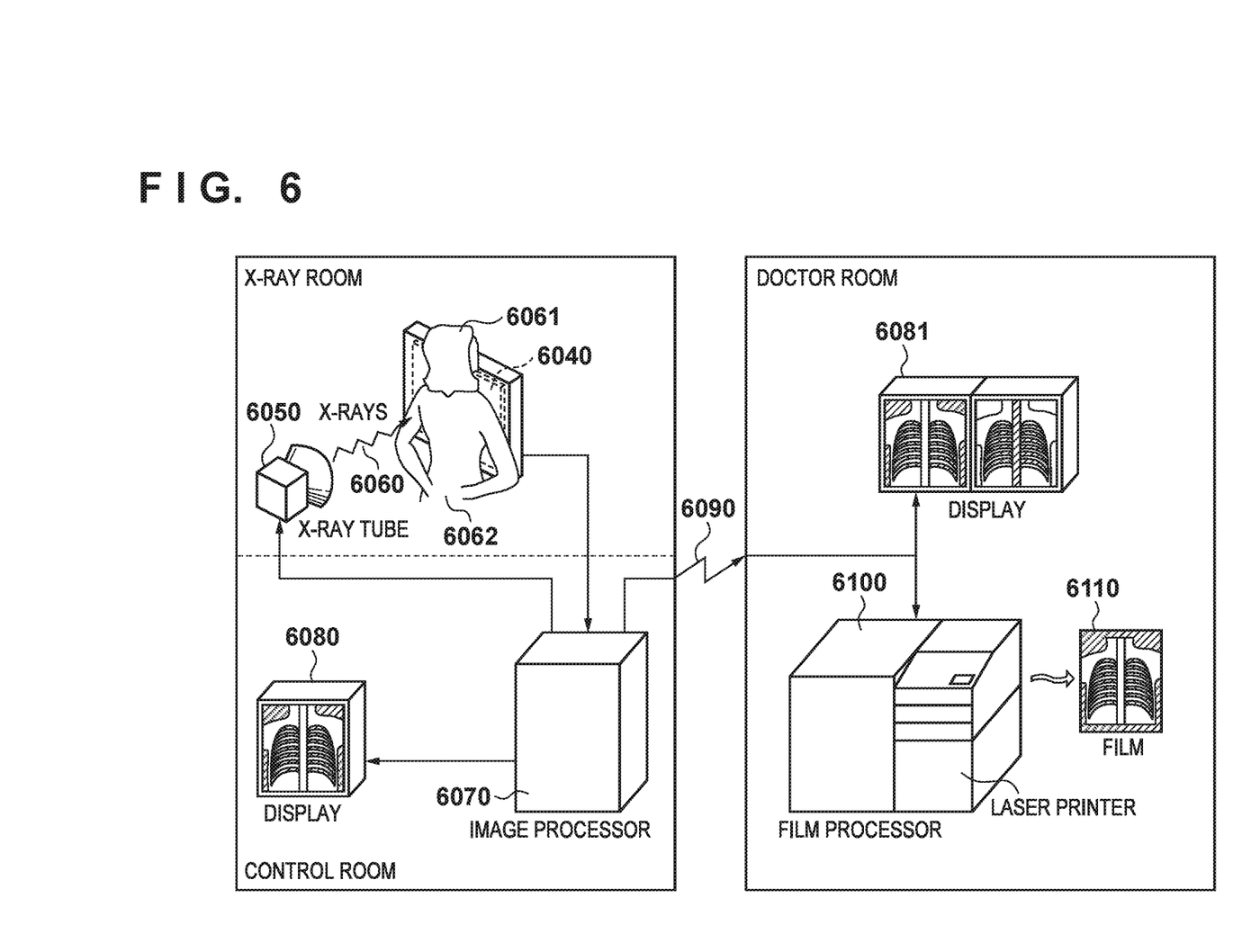
FIG. 6 is a view for explaining an example of the arrangement of a radiation detection system according to some embodiments.

FIG. 6 is a view showing an application example of any one of the radiation detection apparatuses described above to an X-ray diagnostic system (radiation detection system). X-rays 6060 generated by an X-ray tube 6050 (radiation source) are transmitted through a chest region 6062 of an object or a patient 6061 and enter a detection apparatus 6040 as one of the above radiation detection apparatuses. The incident X-rays include information about the inside of the body of the patient 6061. The scintillator emits light as X-rays enter, and electrical information is obtained by photoelectric conversion. This information is converted into a digital signal. An image processor 6070 serving as a signal processing unit performs image processing of the signal. It is possible to observe the resultant image on a display 6080 serving as a display unit in a control room. Note that the radiation detection system includes at least a detection apparatus and a signal processing unit which processes signals from the detection apparatus.

In addition, it is possible to transfer this information to a remote place via a transmission processing unit such as a telephone line 6090. The information can be displayed on a display 6081 as a display unit in another place such as a doctor room or can be stored in a recording unit such as an optical disk. This makes it possible for a doctor in a remote place to perform diagnosis. In addition, a film processor 6100 as a recording unit can record the information on a film 6110 as a recording medium.

Various examples will be described. As each arrangement whose concrete example is not shown in the following examples, any one of the arrangements described above may be used. Embodiment 1 uses a CMOS chip as the sensor panel 110 in the arrangement shown in FIGS. 1A to 1C. The reverse surface of the silicon substrate of the sensor panel 110 is polished to a thickness of 0.3 mm. As the supporting substrate 142, a 1-mm thick CRFP substrate is used. As the scintillator layer 120, CsI:Tl formed by vacuum deposition is used. As the scintillator protective layer 121, a film to which an aluminum sheet is bonded is used. As the frame member 144, a CFRP substrate impregnated with an epoxy resin is used. As the adhesive layer 141, a 100-µm thick silicone-based pressure sensitive adhesive agent is used. As the adhesive layer 143, a two-pack epoxy resin is used.

Example 2 uses a CMOS chip as the sensor panel 110 in the arrangement shown in FIGS. 3A to 3C. The silicon substrate of the sensor panel 110 is polished to a thickness of 0.3 mm. As the supporting substrate 142, a 1-mm thick CRFP substrate is used. As the scintillator layer 120, CsI:Tl formed by vacuum deposition is used. As the scintillator protective layer 121, a film to which an aluminum sheet is bonded is used. As the supporting member 341, an epoxy resin having a compressive strength of 150 MPa is used. As the adhesive layer 141, a 100-µm thick silicone-based pressure sensitive adhesive agent is used.

Example 3 uses a CMOS chip as the sensor panel 110 in the arrangement shown in FIGS. 3A to 3C. The silicon substrate of the sensor panel 110 is polished to a thickness of 0.3 mm. As the supporting substrate 142, a 1-mm thick CRFP substrate is used. As the scintillator layer 120, CsI:Tl formed by vacuum deposition is used. As the scintillator protective layer 121, a film to which an aluminum sheet is bonded is used. As the supporting member 341, 0.2-mm thick stainless steel having compressive strength of 400 Mpa is used. As the adhesive layer 141, a 200-µm thick silicone-based pressure sensitive adhesive agent is used.

Example 4 uses a flat panel as the sensor panel 110 in the arrangement shown in FIGS. 3A to 3C. The glass substrate of the sensor panel 110 is polished to a thickness of 0.3 mm. As the supporting substrate 142, a 1-mm thick CRFP substrate is used. As the scintillator layer 120, polyparaxylylene formed by CVD is used. As the scintillator protective layer 121, a film to which an aluminum sheet is bonded is used. As the supporting member 341, an epoxy resin having a compressive strength of 150 MPa is used. As the adhesive layer 141, a 100-µm thick silicone-based pressure sensitive adhesive agent is used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation detection apparatus comprising:
   a sensor panel having a first surface on which a pixel array and an electrical contact are arranged, and a second surface located on an opposite side to the first surface, the electrical contact being connected by a wiring member through which the pixel array exchanges an electrical signal with an external apparatus;
   a scintillator layer arranged on the first surface side of the sensor panel so as to cover the pixel array;

a supporting substrate including a first supporting portion configured to support the pixel array from the second surface side of the sensor panel through an adhesive layer that functions as a buffer member, the first supporting portion being adhered to the second surface of the sensor panel by the adhesive layer; and a frame member including a second supporting portion fixed to a region in the second surface of the sensor panel located on an opposite to a region of the first surface of the sensor panel on which the electrical contact is arranged so as to support the electrical contact from the second surface side of the sensor panel, the frame member being adhered to the supporting substrate by using an adhesive agent, an elastic modulus of the second supporting portion being higher than an elastic modulus of the adhesive layer functioning as the buffer member, wherein the radiation detection apparatus does not contain a light source on the frame member.

2. A radiation detection system comprising:

the radiation detection apparatus according to claim 1; and signal processing means for processing a signal obtained from the radiation detection apparatus.

3. The apparatus according to claim 1, wherein the second supporting portion is in contact with a region of the second surface of the sensor panel.

4. The apparatus according to claim 1, wherein the sensor panel includes a plurality of sensor chips, and the second supporting portion is formed from a metallic material.

5. The apparatus according to claim 1, wherein the frame member includes a bottom portion to which the supporting substrate is adhered by the adhesive agent and a side wall which is thicker than the bottom portion, the thickness being measured in a direction perpendicular to a plane of the bottom portion, and the side wall is fixed to a region of the second surface of the sensor panel as the second supporting portion.

6. A radiation detection apparatus comprising:

a sensor panel including a plurality of sensor chips, each having a first surface on which a pixel array and an electrical contact are arranged and a second surface located on an opposite side to the first surface, the electrical contact being connected by a wiring member through which the pixel array exchanges an electrical signal with an external apparatus;

a scintillator layer arranged on the first surface side of the plurality of sensor chips so as to cover the pixel arrays of the plurality of sensor chips;

a supporting substrate including a first supporting portion configured to support the pixel arrays of the plurality of sensor chips from the second surface side of the plurality of sensor chips through an adhesive layer that functions as a buffer member, the first supporting portion being adhered to the second surface of the plurality of sensor chips by the adhesive layer; and a frame member including a second supporting portion fixed to regions in the second surfaces of the plurality of sensor chips located on an opposite to regions of the first surfaces of the plurality of sensor chips on which the electrical contacts of the plurality of sensor chips are arranged so as to support the electrical contacts from the second surface side of the plurality of sensor chips, the frame member being adhered to the supporting substrate by using an adhesive agent, an elastic modulus of the second supporting portion being higher than an elastic modulus of the adhesive layer functioning as the buffer member wherein the radiation detection apparatus does not contain a light source on the frame member.

7. The apparatus according to claim 6, wherein the second supporting portion is in contact with regions of the second surfaces of the plurality of sensor chips.

8. The apparatus according to claim 6, wherein the second supporting portion is formed from a metallic material.

9. The apparatus according to claim 6, wherein the frame member includes a bottom portion to which the supporting substrate is adhered by the adhesive agent and a side wall which is thicker than the bottom portion, the thickness being measured in a direction perpendicular to a plane of the bottom portion, and the side wall is fixed to regions of the second surfaces of the plurality of sensor chips as the second supporting portion.

10. A radiation detection system comprising:

the radiation detection apparatus according to claim 6; and signal processing means for processing a signal obtained from the radiation detection apparatus.

* * * * *